US008883877B2

(12) United States Patent
Moszner et al.

(10) Patent No.: US 8,883,877 B2
(45) Date of Patent: *Nov. 11, 2014

(54) MATERIALS BASED ON RADICALLY POLYMERIZABLE N,O-FUNCTIONALIZED ACRYLIC ACID HYDROXAMIDES

(75) Inventors: Norbert Moszner, Triesen (LI); Iris Lamparth, Grabs (CH); Urs Karl Fischer, Arbon (CH); Frank Zeuner, Schellenberg (LI); Armin de Meijere, Gottingen (DE); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 374 days.

This patent is subject to a terminal disclaimer.

(21) Appl. No.: 13/008,064

(22) Filed: Jan. 18, 2011

(65) Prior Publication Data

US 2011/0130486 A1    Jun. 2, 2011

Related U.S. Application Data

(62) Division of application No. 11/898,338, filed on Sep. 11, 2007, now Pat. No. 7,932,303.

(30) Foreign Application Priority Data

Mar. 15, 2007    (EP) .................... 07005396

(51) Int. Cl.
 *A61K 6/08*    (2006.01)
 *A61K 6/083*    (2006.01)
 *A61K 6/00*    (2006.01)

(52) U.S. Cl.
 CPC ............. *A61K 6/0023* (2013.01); *A61K 6/0017* (2013.01); *A61K 6/083* (2013.01)
 USPC ........... 523/116; 523/115; 523/118; 433/226; 433/228.1; 106/35

(58) Field of Classification Search
 USPC ............... 523/116, 115, 118; 433/226, 228.1; 106/35
 See application file for complete search history.

(56) References Cited

U.S. PATENT DOCUMENTS

| 3,660,343 | A | 5/1972 | Saffir |
| 3,833,518 | A | 9/1974 | Rubin et al. |
| 3,926,870 | A | 12/1975 | Keegan et al. |
| 5,011,868 | A | 4/1991 | Keegan |
| 5,068,264 | A | 11/1991 | Muller et al. |
| 6,953,832 | B2 * | 10/2005 | Moszner et al. .............. 528/310 |
| 7,932,303 | B2 * | 4/2011 | Moszner et al. .............. 523/116 |
| 2005/0130063 | A1 * | 6/2005 | Matsumoto et al. ....... 430/270.1 |

FOREIGN PATENT DOCUMENTS

| CA | 2250333 | 10/1998 |
| GB | 1039750 | 7/1965 |
| WO | WO 03/035013 | 5/2003 |

OTHER PUBLICATIONS

Shinya Kitoh and Mikio Miyake, "Studies on Adhesive Monomers for Teeth. V. Influence of Substitutents in Methacrylamide Derivatives." Journal of Applied Polymer Science, vol. 39, 103-108 (1990).
Shinya Kitoch, Kunitomo Suzuki, Takao Kiyohara, and Keisuke Kurita, "Adhesive Monomers to Dental Ceramics. II. Methacrylamide Derivatives Continaing Carboxyl and Phenyl Groups for Effective Adhesion of Calcium Metaphosphate Ceramic." Journal of Applied Polymer Science, vol. 51, 2021-2025 (1994).
Nobuo Nakabayashi, PhD, "Hybridization of Dental Hard Tissues," Quintessence Publishing Co., Ltd., 1998, pp. 9-14.
H. Goldwhite and B.C. Saunders, "Esters Containing Phosphorus. Part XIV. Some tert.-Buty! Esters and Their Reactions," J. Chem. Soc, 1957, pp. 2409-2412.
Tadeusz Gajda and Andrezej Zwierzak, "Phase-Transfer-Catalysed Halogenation of Di-t-buty! Phosphite. Preparation of Di-t-buty! Phosphorahalidates," Syntheses, 1976, pp. 243-244.
Norbert Moszner, Frank Zeuner, Jorg Angermann, Urs Karl Fischer, Volker Rheinberg, "Monomers for Adhesive Polymers, 4, Synthesis and Radical Polymerization of Hydrolytically Stable Crosslinking Monomers," Macromol. Mater. Eng. 2003, 288 No. 8, pp. 621-628.
Norbert Moszner, Urs Karl Fischer, Jorg Angermann, Volker Rheinberger, "Bis-(acrymalide)s as new corss-linkers for resin-based composite restoratives," Dental Materials 22, Academy of Dental Materials by Elsevier Ltd., 2005, pp. 1157-1162.
M. Mentzel and H.M.R. Hoffman, "N-Methoxy-N-methylamides (Weinrab Amides) in Modern Organic Synthesis," Journal fur praktische Chemie Chemiker-Zeitung, 1997, pp. 517-524.
Wataru Kurosawa, Toshiyuki Kan, and Tohru Fukuyama, "Preparation of Secondary Amines From Primary Amines Via 2-Nitrobenzenesulfonamides:    N-(4-Methoxybenzyl)-3-Phenylpropylamine," Organiz Syntheses, Coll. vol. 10, p. 482 (2004); vol. 79, p. 186 (2002).
Edward Grochowski, Janusz Jurczak, "A New Syntheses of O-Alkylhydroxylamines," Institute of Organic Chemistry, Polish Academy of Sciences, 01-224 Warszawa, Poland, pp. 682-684, Oct. 1976.
Shun Su, Joshua R. Giguere, Scott E. Schaus and John A. Porco, Jr., "Syntheses of complex alkoxyamines using a polymer-supported N-hydroxyphthalimide," Department of Chemistry and Center for Chemical Methodology and Library Development Metcalf Center for Science and Engineering, Boston University, 2004, pp. 8646-8657.
K.H. Buchel, J. Falbe, H. Hagemann, M. Hanack, D. Klamann, R. Kreher, H. Kropf, M. Regitz, "Methoden Der Organischen Chemie, Erweiterungs—Und Folgebande zur Vierten Auflage," Houben-Weyl, vol. E5 1985, Georg Thieme Verlag.
U.K. Fischer, N. Moszner, F. Zeuner, V. Rheinberger, "Tagunsband der GDCh-Fachgruppentagung Polymers & Coatings," (conference booklet on the German Chemical Society), Sep. 24-26, 2006, Mainz, p. 82.

* cited by examiner

*Primary Examiner* — Michael Pepitone
(74) *Attorney, Agent, or Firm* — Ann M. Knab; Thad McMurray

(57) ABSTRACT

The present invention relates to a dental material comprising, relative to the total mass of the material:
 (a) 1 to 95 wt.-% of at least one polymerizable N,O-functionalized acrylic acid hydroxamide,
 (b) 0 to 70 wt.-% diluent monomer,
 (c) 0 to 70 wt.-%, cross-linker monomer,
 (d) 0.1 to 5.0 wt.-% polymerization initiator
 (e) 0 to 80 wt.-% filler,
 (f) 0 to 70 wt.-% solvent, and
 (g) 0 to 70 wt.-% adhesive monomer.

11 Claims, No Drawings

MATERIALS BASED ON RADICALLY POLYMERIZABLE N,O-FUNCTIONALIZED ACRYLIC ACID HYDROXAMIDES

This application is a divisional application of U.S. application Ser. No. 11/898,338, filed Sep. 11, 2007, now U.S. Pat. No. 7,932,303, which claims priority pursuant to 35 U.S.C. §119, to European Patent Application No. 07005396.2 filed Mar. 15, 2007, all of which are incorporated herein by reference.

FIELD

According to certain aspects, the present invention relates to radically polymerizable, N,O-functionalized acrylic acid hydroxamides as cross-linkers and/or adhesive monomers. According to additional aspects, the present invention also relates to dental materials, adhesives, coatings or composites comprising radically polymeriable N,O-functionalized acrylic acid hydroxamides as cross-linkers and/or adhesive monomers.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Amides of acrylic or methacrylic acid are known as comonomers for the preparation of polymers for prostheses (GB-A-1 039 750) or denture adhesives (DE-A-2 316 603, U.S. Pat. No. 3,926,870, U.S. Pat. No. 5,011,868). Furthermore, selectively substituted acrylamides or methacrylamides are suitable as effective adhesion components in dental adhesives, which for example are the subject of U.S. Pat. No. 3,660,343 or EP-A-0 394 792 or have been described by S. Kitoh et al (cf. J. Appl. Polym. Sci. 39 (1990) 103, J. Appl. Polym. Sci. 51 (1994) 2021). Finally, because of their improved hydrolysis stability compared with conventional dimethacrylate cross-linkers, multifunctional (meth)acrylamides are particularly suitable as cross-linkers for aqueous-acid enamel-dentine adhesives (cf. N. Moszner, F. Zeuner, J. Angermann, U. K. Fischer, V. Rheinberger, Macromol. Mater. Eng. 288 (2003) 621; U.S. Pat. No. 6,953,832) and also for self-adhesive composites (cf. N. Moszner, U. K. Fischer, J. Angermann, V. Rheinberger, Dent. Mater. 22 (2006) 1157).

N-alkoxy-N-alkylamides, also called Weinreb amides, are intermediate products established in modern organic synthesis chemistry, e.g., for the synthesis of sterically demanding ketones or as substrate for enantioselective Diels-Alder reactions (M. Mentzel, H. M. R. Hoffmann, J. prakt. Chem. 330 (1997) 517). Weinreb amides can be accessed easily, e.g., by acylation of N,O-dimethylhydroxylamine with the corresponding acid chloride. The Weinreb amides are also characterized by a considerable stability and can accordingly be purified by customary methods, e.g., by crystallization, distillation or chromatography. Above all the N-methoxy-N-methyl acrylamide is known as polymerizable N,O-functionalized carboxylic acid hydroxamide (cf. U. K. Fischer, N. Moszner, F. Zeuner, V. Rheinberger, Tagungsband der GDCh-Fachgruppentagung Polymers & Coatings (conference booklet of the German Chemical Society), Sep. 24-26, 2006, Mainz, p. 82). On the other hand, the use of polymerizable, N,O-functionalized acrylic acid hydroxamides for the preparation of dental materials is not described.

SUMMARY

According to certain aspects, the invention provides a material which can be very quickly cured by means of radical polymerization. Thus, in certain embodiments, a cross-linking material (composite or coating) and/or material adhering to a hard tooth substance (adhesive, composite or coating) formed which can be particularly suitable for dental purposes.

According to further aspects of the invention, a material is provided which is characterized in that it contains at least a polymerizable N,O-functionalized acrylic acid hydroxamide of the general Formula (I)

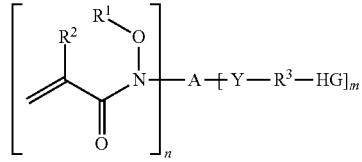

Formula (I)

in which

A is an n+m-valent linear or branched aliphatic $C_1$ to $C_{50}$ radical, in which the carbon chain can be interrupted by O, S, —CO—O—, CO—NH, O—CO—NH or NH—CO—NH, an n+m-valent aromatic $C_6$ to $C_{18}$ radical or an n+m-valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical and n is a number from 1 to 5 and m a number from 0 to 3.

The present invention also includes the use of an amide of the general Formula (I) as a dental material or for the preparation of a dental material, i.e., of a material for use as a dental material.

As used herein, dental materials according to the invention include dental adhesives, a dental coating materials, a dental filling materials, dental cements, an indirect or direct restorative for dental inlays, dental onlays, dental veneering materials for crowns and bridges, dental materials for artificial teeth or other applications in prosthetic, preservative and preventive dentistry as finished articles, raw materials or components thereof.

DETAILED DESCRIPTION

Polymerizable N,O-functionalized acrylic acid hydroxamides of the general Formula (I) represent monomers of different type and reactivity which, optionally in mixtures with other polymerizable components, by copolymerization in the presence of suitable radical initiators, thermally or upon irradiance of light of the visible, UV or IR range, result in mechanically stable coatings or shaped bodies. The selection and number of the polymerizable or functional groups allows a distinction to be made between different types of the polymerizable N,O-functionalized acrylic acid hydroxamides according to of the general Formula (I):

n=1, m=0: monofunctional N,O-functionalized acrylamides,
n=2-5, m=0: multifunctional N,O-functionalized acrylamides which can be used as cross-linkers,
n=1, m=1: monofunctional N,O-functionalized acrylamides which carry an acid adhesion group,
n=2-5, m=1: cross-linking, multifunctional N,O-functionalized acrylamides which carry an acid adhesion group and
n=2-5, m=2-3: cross-linking, multifunctional N,O-functionalized acrylamides which possess several acid adhesion groups.

Thus, depending on the selection of the polymerizable N,O-functionalized acrylic acid hydroxamides of the general Formula (I), materials with different properties and different dental applications can be prepared.

Thus the multifunctional N,O-functionalized acrylic acid amides (n=2-5, m=0) are suitable as a cross-linker component particularly for composites or cements, wherein the cross-linking density or the mechanical properties, such as elastic modulus, of the cured materials increase or improve with increasing functionality, i.e., with increasing n. The cross-linking density of such materials can also be reduced by copolymerization with monofunctional N,O-functionalized acrylic acid amides (n=1, m=0).

Monofunctional, N,O-functionalized acrylamides which carry an acid adhesion group (n=1, m=1) can be used as adhesive monomers in the preparation of adhesives. Through the selective addition of multifunctional, cross-linking N,O-functionalized acrylic acid amides to these adhesives their rate of curing can be increased, wherein as a result of the cross-linking the swellability of the adhesive coat decreases and its strength increases.

Alternatively, above all the cross-linking, multifunctional N,O-functionalized acrylic acid amides which carry an acid adhesion group (n=2-5, m=1) or even the cross-linking, multifunctional N,O-functionalized acrylic acid amides which possess several acid adhesion groups (n=2-5, m=2-3) can be used for such rapidly curing adhesives.

Finally, the N,O-functionalized acrylic acid amides which carry one or more acid adhesion groups and contain one or more N,O-functionalized acrylic acid amide radicals can be used as a component of dental composites, cements or coating materials. The corresponding materials then show self-adhesive properties.

The N,O-functionalized acrylamides of the general Formula (I) can be prepared by reaction of N,O-functionalized amines with acrylic acid halides ($CH_2=CR^2COX$, X=Cl or Br) using the methods known from organic chemistry for forming amide bonds (cf. Methoden der Organischen Chemie, HOUBEN-WEYL Vol. E5 1985, Georg Thieme Verlag p. 941 ff.):

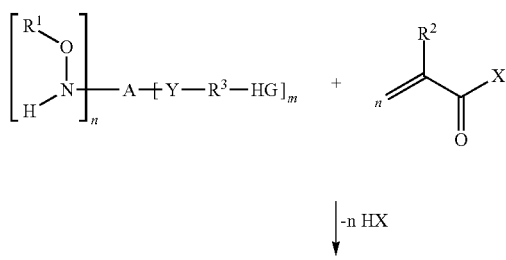

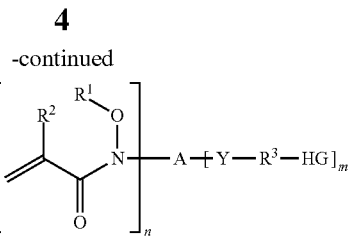

The corresponding acid chlorides are preferably used in the presence of equimolar quantities of auxiliary base, e.g., triethylamine or pyridine (in the following specific example $R^1=CH_3$, $R^2=H$, $A=C_6H_{12}$, n=2; Y, $R^3$ and HG are dispensed with.):

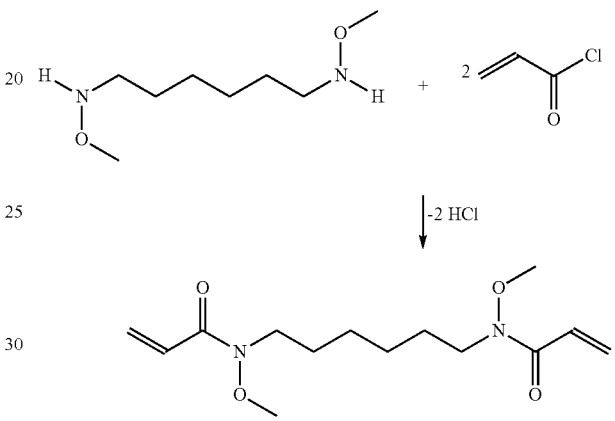

The secondary N-methoxyamines used here can be prepared via the 2-nitrobenzenesulfonyl protective group analogously to the synthesis of secondary amines (cf. W. Kurosawa, T. Kan, T. Fukuyama, Org. Synth. 79 (2002) 186). For example, the above 1,6-Di(N-methoxyamino)hexane can be obtained by the reaction of 1,6-dibromohexane with N-methoxy-2-nitrobenzenesulfamide and deprotection of the formed sulfamide with thiophenol (Ph-SH). The required methoxy-2-nitrobenzenesulfamide can be synthesized easily by reacting O-methylhydroxylamine hydrochloride with 2-nitrobenzene sulfonyl chloride:

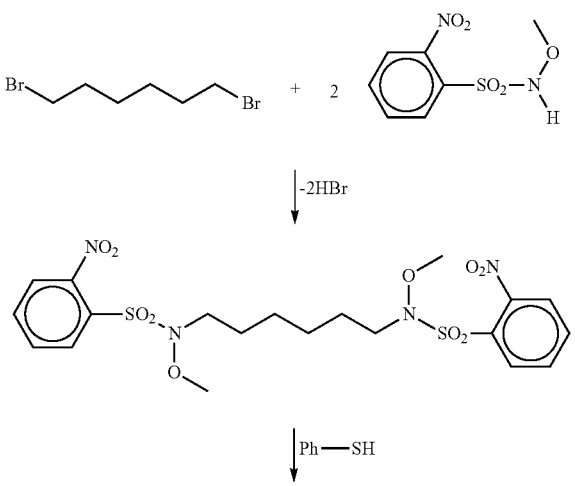

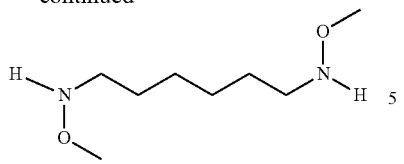
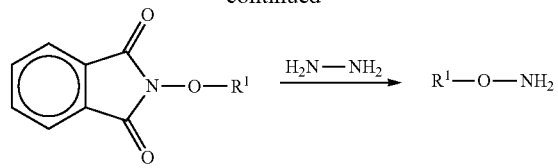

Analogously other hydroxylamine derivatives of the general structure $R^1$—O—$NH_2$ can also be reacted. These hydroxylamine derivatives can be prepared by reacting the corresponding alcohols $R^1$—OH with triphenylphosphine (($Ph)_3P$), N-hydroxyphthalimide and diisopropyl-azodicarboxylate (DIAD) and then hydrazinolysis of the formed phthalimide derivative (cf. E. Grochowski, J. Jurczak, Synthesis 1976, 682; S. Su, J. R. Giguere, S. E. Schaus, J. A. Porco, Tetrahedron 60 (2004) 8645):

If N,O-functionalized acrylamides of the general Formula (I) are prepared which carry one or more acid groups HG, thus likewise the use of the correspondingly usual protective group technique is necessary. Accordingly it is advantageous not to split off the acid function from the protective groups until the last synthesis step. For example, N,O-functionalized acrylamides with a phosphonic acid function (e.g., $R^1$=$CH_3$, $R^2$=H, HG=—P=O(OH)$_2$, n and m=1, A=alkylene, $R^3$ and Y are not present) can be prepared such that initially a α,ω-halogenalkylene phosphonic acid di-tert-butylester (tert-butyl group=protective group, X=halogen such as Cl or Br) is reacted with N-methoxy-2-nitrobenzenesulfamide. By deprotecting the formed sulfamide and then reacting the N-methoxyamino group with acrylic acid chloride the N,O-functionalized acrylic acid amide forms, the phosphonic acid group of which is released after splitting off the two tert-butyl protective groups with trifluoroacetic acid (TFA).

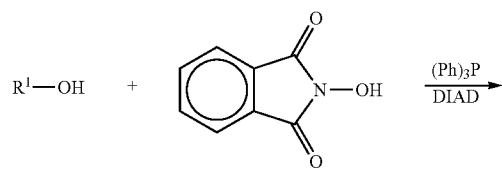

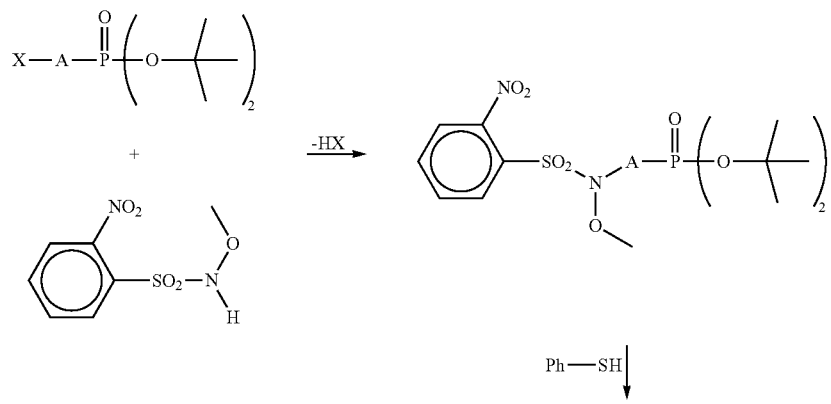

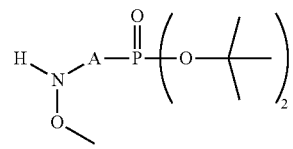

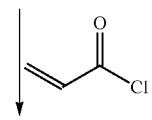

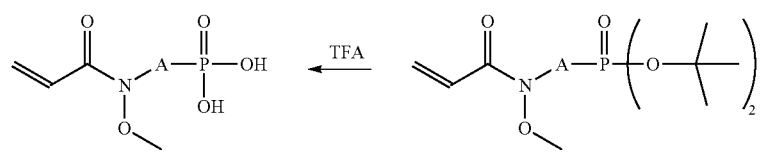

In one embodiment of the invention the one or more substituents at the radical A are selected from the group comprising $C_1$ to $C_5$ alkyl groups, Cl, Br and OH, in particular $C_1$ to $C_3$ alkyl groups and OH. The one or more substituents at the radical $R^1$ are selected from the group comprising Cl, Br and OH.

A material according to the invention based on an N,O-functionalized acrylic acid amide of the general Formula (I) is one in which A is an n+m-valent linear or branched aliphatic $C_1$ to $C_{30}$ radical, e.g., a $C_1$ to $C_{15}$ radical or a $C_1$ to $C_{10}$ radical, in which the carbon chain can be interrupted by O, —OO—O— or O—CO—NH, an n+m-valent aromatic $C_6$ to $C_{10}$ radical, or an n+m-valent cycloaliphatic $C_3$ to $C_{18}$ radical, wherein the radicals can carry one or more substituents, Y is not present, or is O, an ester or urethane group, $R^1$ is an aliphatic $C_1$ to $C_8$ alkyl or cycloalkyl radical, e.g., a $C_1$ to $C_4$ alkyl or cyclohexyl radical, $R^2$ is H or $CH_3$, $R^3$ is not present or is a $C_1$ to $C_{12}$ alkylene radical which can be interrupted by O, e.g., a $C_6$ to $C_{12}$ alkylene radical, HG is not present, is —COOH, —P=O(OH)$_2$, —O—P=O(OH)$_2$, —SO$_2$OH or —O—P=O(OH)(OR$^4$), $R^4$ is a $C_1$ to $C_4$ alkyl radical, e.g., methyl, ethyl, propyl or butyl, n is a number from 1 to 3 and m a number from 0 to 2.

A further material according to the invention based on an N,O-functionalized acrylic acid amide of the general Formula (I) is one in which A is an n+m-valent linear or branched aliphatic $C_1$ to $C_{12}$ radical, e.g., $C_1$ to $C_{10}$ alkyl or $C_1$ to $C_{12}$ alkylene, an n+m-valent cycloaliphatic $C_6$ to $C_{12}$ radical or an n+m-valent aromatic $C_6$ to $C_{10}$ radical, Y is not present or is an ester group, $R^1$ is a $C_1$ to $C_4$ alkyl, $R^2$ is H or $CH_3$, $R^3$ is not present or is a $C_4$ to $C_8$ alkylene radical which can be interrupted by O, HG is not present, or is —COOH, —P=O(OH)$_2$, —OP=O(OH)$_2$, —OP=O(OH)(OC$_2$H$_5$) or —SO$_2$OH, n is 1, 2 or 3 and m is 0 or 1.

One particular material according to the invention based on an N,O-functionalized acrylic acid amide of the general Formula (I) is one in which A is an n+m-valent linear or branched aliphatic $C_1$ to $C_5$ radical such as ethyl, propyl, butyl, ethylene, propylene, butylene, pentylene or pentanetriyl, an n+m-valent cycloaliphatic $C_6$ radical such as cyclohexyl, cyclohexylene, cyclohexantriyl, or an n+m-valent aromatic $C_6$ radical such as phenyl or benzenetriyl, Y is not present or is —COO—, $R^1$ is methyl, ethyl or propyl, $R^2$ is H or $CH_3$, $R^3$ is not present or is pentylene, HG is dispensed with, is —COOH, —P=O(OH)$_2$, —OP=O(OH)$_2$, —OP=O(OH)(OC$_2$H$_5$) or —SO$_2$OH, n is 1, 2 or 3 and m is 0 or 1.

A N,O-functionalized acrylic acid amide of the general Formula (I) according to one embodiment of the invention, A can mean unsubstituted $C_6$ alkylene, $R^1$ methyl, $R^2$ H and n=2, wherein m=0. Alternatively A can preferably mean unsubstituted $C_{10}$ alkylene, $R^1$ methyl, $R^2$ H, n and m each=1 and HG —OP=O(OH)$_2$, wherein the radicals Y and $R^3$ are not present.

Specific examples of the N,O-functionalized acrylic acid amides of the general Formula (I) according to the invention, include, among others:

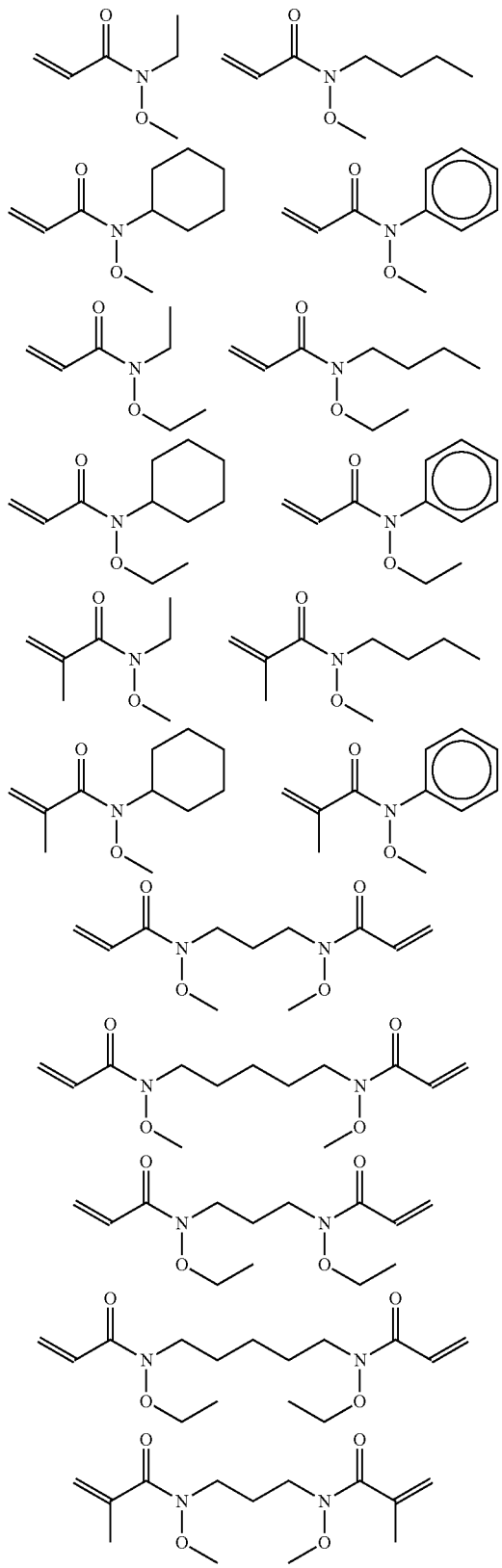

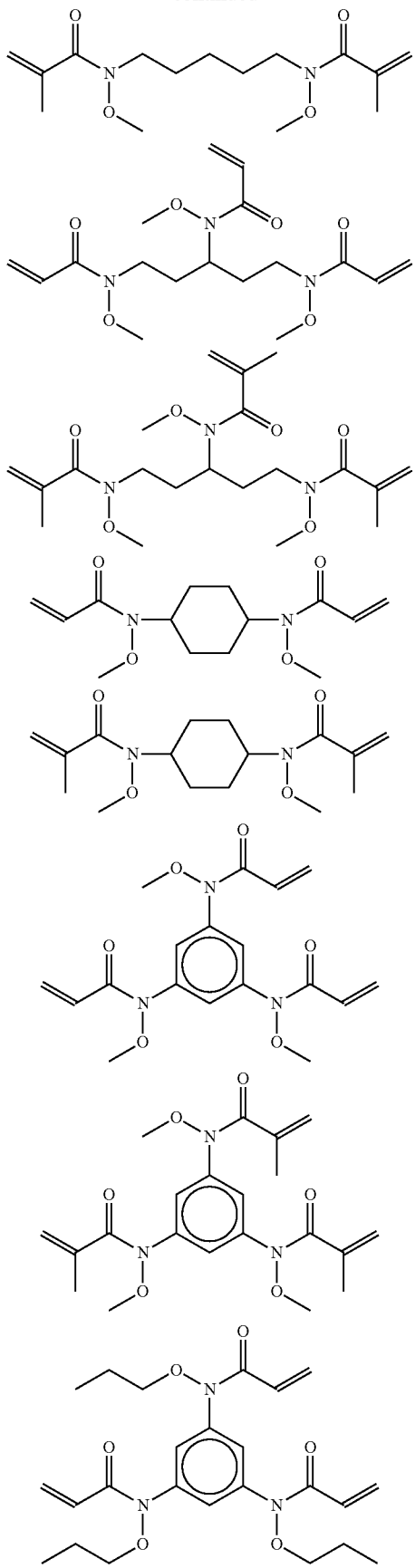
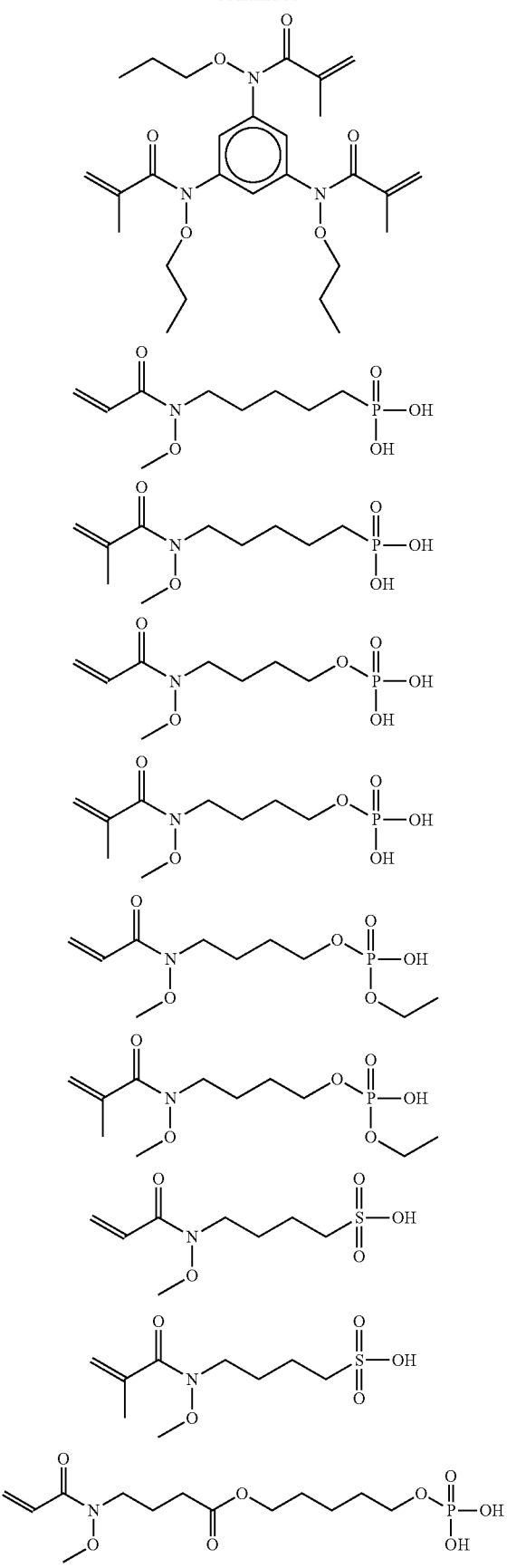

-continued

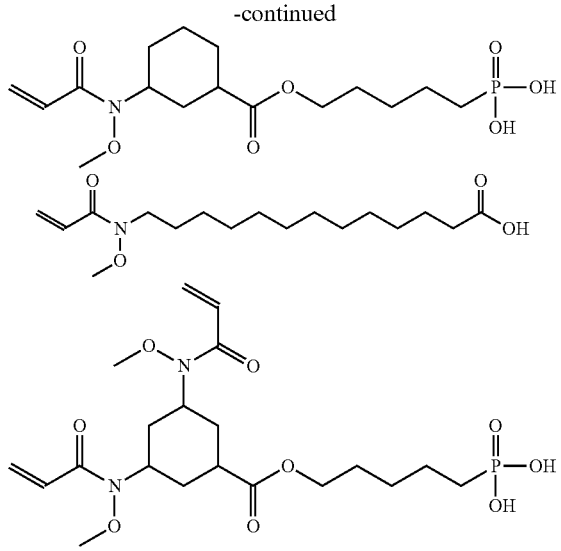

To prepare materials according to the invention, the N,O-functionalized acrylic acid amides alone, their mixtures with one another or their mixtures with other diluent monomers or cross-linker monomers are cured by radical polymerization. Before polymerization, in addition to the initiator, possibly suitable solvents or further additives, such as fillers, stabilizers or other adhesive monomers, can be added.

Suitable radically polymerizable diluent monomers mono (meth)acrylamides and/or mono(meth)acrylates, e.g., acrylamide, methacrylamide, N-ethylacrylamide, methyl, ethyl, butyl, benzyl, furfuryl or phenyl(meth)acrylate. As further cross-linker monomers, known multifunctional acrylates or methacrylates, such as e.g., bisphenol-A-di(meth)acrylate, Bis-GMA (an addition product of methacrylic acid and bisphenol-A-diglycidylether), UDMA (an addition product of 2-hydroxyethyl methacrylate and 2,2,4-hexamethylenediisocyanate), di-, tri- or tetraethylene glycol di(meth)acrylate, decanediol di(meth)acrylate, trimethylene propane tri(meth)acrylate, pentaerythritol tetra(meth)acrylate and butanediol di(meth)acrylate, 1,10-decanediol di(meth)acrylate or 1,12-dodecanediol di(meth)acrylate, can be used.

The compositions based on N,O-functionalized acrylamides are cured after suitable initiators have been added by thermal, photochemical or redox-induced radical polymerization. Examples of thermal initiators are the known peroxides, such as, e.g., dibenzoyl peroxides, dilauryl peroxides, tert-butylperoctoate or tert-butylperbenzoate and further azobisisobutyroethyl ester, azobisisobutyronitrile, azobis-(2-methylpropionamidine)dihydrochloride, benzopinacol or 2,2-dimethyl benzopinacol.

Examples of suitable photoinitiators are dibenzoyl diethyl germanium or dibenzoyl dimethyl germanium, benzophenone, benzoin and their derivatives or α-diketones or their derivatives such as 9,10-phenanthraquinone, diacetyl or 4,4-dichlorobenzene. Particularly, camphorquinone and 2,2-dimethoxy-2-phenyl-acetophenone and more particularly α-diketones in combination with amines as a reductant, such as e.g., 4-(N,N-dimethylamino)-benzoic acid ester, N,N-dimethylaminoethyl methacrylate, N,N-dimethyl-sym.-xylidine or triethanolamine are used. In addition, acylphosphines, such as e.g., 2,4,6-trimethylbenzoyldiphenyl or bis(2,6-dichlorobenzoyl)-4-N-propyl phenyl phosphinic oxide are also particularly suitable.

Redox-initiator combinations, such as e.g., combinations of benzoyl or lauryl peroxide with N,N-dimethyl-sym.-xylidine or N,N-dimethyl-p-toluidine, are used as initiators for a polymerization carried out at room temperature.

The N,O-functionalized acrylic acid amide cross-linkers are particularly suitable as a cross-linking component of solutions of known strongly acidic adhesive monomers. These include phosphoric acid ester methacrylates, such as e.g., 2-(methacryloyloxy)ethyl dihydrogen phosphate, di-[2-(methacryloyloxy)ethyl]hydrogen phosphate or dipentaerythritol pentamethacryloyloxy-dihydrogen phosphate (cf. N. Nakabayashi, P. D. Pashley, Hybridization of dental hard tissues, Quintess. Publ. Tokyo etc. 1998, 9 ff), and hydrolysis-stable acrylphosphonic acids, such as, e.g. 2-[3-(dihydroxyphosphoryl)-oxa-propyl]acrylic acid ethyl ester or 1,2-bis[1-dihydroxyphosphoryl)-1-[2-methylene-3-ylpropanic acid ethyl ester)oxy]methyl]-benzene, which are described in DE-A-197 46 708, are particularly suitable.

Above all polar solvents, such as water, ethanol, acetone, acetonitrile or mixtures of these solvents can be used as solvents for the N,O-functionalized acrylic acid amides.

Optionally, the compositions according to the invention can contain further additives, such as colorants (pigments or dyestuffs), stabilizers, aromatics, microbiocidal active ingredients, plasticizers or UV absorbers.

Furthermore the compositions according to the invention can be filled with inorganic particles or fibres to improve the mechanical properties. Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or microfine fillers such as pyrogenic silicic acid or precipitation silicic acid and macro- or microfillers such as quartz, glass ceramic or glass powder with an average particle size of 0.01 to 5 µm and x-ray opaque fillers, such as ytterbium trifluoride.

A composition according to the invention may contain, in each case relative to the total mass of the material:
(a) 1 to 95 wt.-% acrylamide of the general Formula (I),
(b) 0 to 70 wt.-% diluent monomer,
(c) 0 to 70 wt.-% cross-linker monomer,
(d) 0.1 to 5.0 wt.-% polymerization initiator
(e) 0 to 80 wt.-% filler,
(f) 0 to 70 wt.-% solvent, and
(g) 0 to 70 wt.-% adhesive monomer.

By diluent monomer and cross-linker monomer are meant monomers which do not fall under Formula (I). By adhesive monomer are meant monomers which have one or more acid adhesion groups and fall under the Formula (I) or not.

A further composition according to the invention contains, in each case relative to the total mass of the material:
(a) 5 to 70 wt.-% acrylamide of the general Formula (I),
(b) 0 to 40 wt.-% diluent monomer,
(c) 0 to 40 wt.-% cross-linker monomer,
(d) 0.2 to 2.0 wt.-% polymerization initiator
(e) 0 to 50 wt.-% filler,
(f) 0 to 50 wt.-% solvent, and
(g) 0 to 50 wt.-% adhesive monomer.

A composition according to the invention usable as dental adhesive contains, in each case relative to the total mass of the material:
(a) 5 to 40 wt.-%, in particular 10 to 40 wt.-% acrylamide of the general Formula (I),
(b) 0 to 40 wt.-% diluent monomer,
(c) 0 to 70 wt.-%, in particular 50 to 70 wt.-% cross-linker monomer, and
(d) 0.2 to 2.0 wt.-% polymerization initiator,
(e) 2 to 50 wt.-%, in particular 20 to 50 wt.-% solvent, (f) 5 to 40 wt.-%, in particular 10 to 40 wt.-% adhesive monomer, (g) 0 to 20 wt.-% nanofiller (filler with a primary particle size of <50 nm).

A composition according to the invention usable as dental cement contains, in each case relative to the total mass of the material:

(a) 5 to 20 wt.-% acrylamide of the general Formula (I), (b) 0 to 20 wt.-% diluent monomer, (c) 0 to 20 wt.-% cross-linker monomer, (d) 0.2 to 2.0 wt.-% polymerization initiator, (e) 5 to 60 wt.-% filler, and (f) 2 to 20 wt.-% adhesive monomer.

A composition according to the invention usable as dental filling material contains, in each case relative to the total mass of the material:

(a) 5 to 20 wt.-% acrylamide of the general Formula (I), (b) 0 to 30 wt.-% diluent monomer, (c) 0 to 30 wt.-% cross-linker monomer, (d) 0.2 to 2.0 wt.-% polymerization initiator, and (e) 10 to 80 wt.-%, in particular 50 to 80 wt.-% solvent.

A composition according to the invention usable as dental coating material contains, in each case relative to the total mass of the material:

(a) 5 to 40 wt.-% acrylamide of the general Formula (I), (b) 0 to 50 wt.-% diluent monomer, (c) 0 to 50 wt.-% cross-linker monomer, (d) 0.2 to 2.0 wt.-% polymerization initiator, (e) 2 to 50 wt.-% solvent, and (f) 0 to 20 wt.-% nanofiller (filler with a primary particle size of <50 nm).

The invention is described in further detail below with reference to the following illustrative, non-limiting examples.

Example 1

Synthesis of 1,6-bis(N-acryloyl-N-methoxyamino)hexane $1^{st}$ stage: N-methoxy-2-nitrobenzenesulfonamide (1)

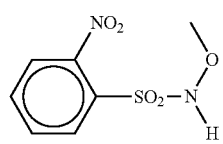

2-nitrobenzene sulfonyl chloride (28.8 g, 130 mmol) was added within 30 min to a solution of O-methylhydroxylamine hydrochloride (11.7 g, 141 mmol) in pyridine (100 ml) accompanied by stirring and water cooling. After the addition the mixture was stirred for a further 30 min at room temperature (RT), mixed with ice (200-300 g) and acidified with concentrated HCl to pH 2-3. The still-cold suspension was sucked out, the precipitate carefully washed with ice water and dried. 26.4 g (87%) of the sulfamide 1 was obtained as a yellowish solid with a melting point of 133-136° C. $^1$H-NMR (DMSO-D$_6$, 300 MHz): δ=3.67 (s, 3H), 7.92-8.06 (m, 4H), 11.05 (s, 1H) ppm.

$2^{nd}$ Stage: N,N'-dimethoxy-2,2'-dinitrohexamethylene di(benzenesulfamide) (2)

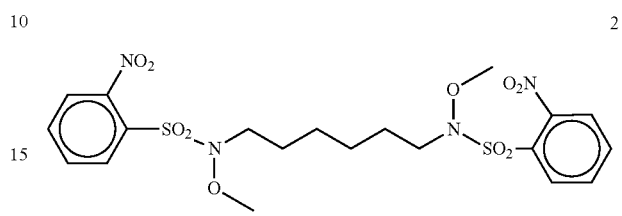

A mixture of the sulfamide 1 (24.1 g, 104 mmol), 1,6-dibromohexane (12.2 g, 5.0 mmol) and K$_2$CO$_3$ (17.0 g, 123 mmol) in DMF (100 ml) was stirred intensively at 70-80° C. for 3 h, cooled and approximately 5 times the volume of water added to it. After dilution with water the crude product precipitated out as deposit. It was sucked off, washed with plenty of water and dissolved in CH$_2$Cl$_2$ (approx. 500 ml). The solution was dried over anhydrous MgSO$_4$ and concentrated under vacuum to approximately one quarter of the volume. Approximately the same volume of hexane was added to the residue, sucked off after standing in the refrigerator for 1 h, washed with a 1:1 mixture of methylene chloride and hexane and dried. 26.1 g (96%) of the sulfonamide 2 was obtained as an almost colourless solid with a melting point of 145-146° C. $^1$H-NMR (DMSO-D$_6$, 300 MHz): δ=1.37 (m$_c$, 4H), 1.59 (m$_c$, 4H), 2.99 (t, J=7 Hz, 4H), 3.77 (s, 6H), 7.86-7.92 (m, 2H), 7.97-8.02 (m, 6H) ppm.

$3^{rd}$ stage: 1,6-di(N-methoxyamino)hexane (3)

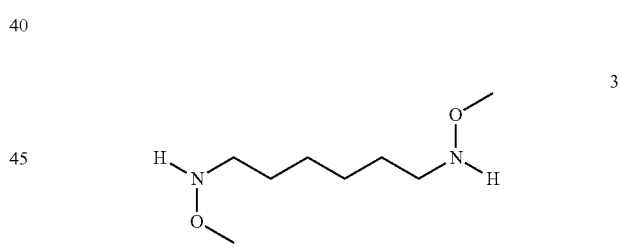

A mixture of the sulfamide 2 (28.1 g, 51.4 mmol), K$_2$CO$_3$ (43 g, 312 mmol) and thiophenol (22.6 g, 206 mmol) in DMF (150 ml) was stirred intensively for 2-6 h at 40-45° C. (DC control). For working-up, the mixture was diluted with approximately 2 times the volume of water and ether. The cooled solution was very carefully acidified with concentrated HCl (CO$_2$ formation, thiophenol) and the acid aqueous phase was separated off. The organic phase was washed again with 5% HCl (2×100 ml). The combined acid phases were washed with ether (2×100 ml), cooled with ice water and very carefully made strongly alkaline with solid KOH (vigorous build-up of heat). The product was precipitated out as a yellow-orange oil. This was extracted with ether (3×50 ml), the solution dried over K$_2$CO$_3$ and concentrated under vacuum. 8.48 g (89%) of the diamine 3 was obtained. For final purification this diamine was distilled under vacuum almost without losses, boiling point 95-97° C. (0.5 Torr). $^1$H-NMR (CDCl$_3$, 300 MHz): δ=1.33 (m$_c$, 4H), 1.47 (m$_c$, 4H), 2.87 (t, J=7 Hz, 4H), 3.50 (s, 6H), 5.49 (br. s, 2H) ppm.

4$^{th}$ stage:
1,6-bis(N-acryloyl-N-methoxyamino)hexane (4)

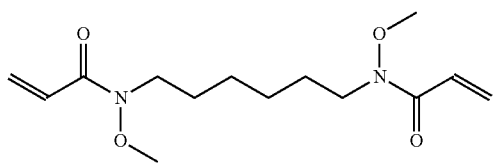

Acrylic acid chloride (996 mg, 11 mmol) was added dropwise within 5 min to a stirred suspension of the bis-methoxyamine 3 (881 mg, 5 mmol), Na$_2$CO$_3$ (2.65 g, 25 mmol) and BHT (=2,6-tert-butyl-4-methylphenol) (10 mg) in anhydrous diethylether (100 ml) accompanied by ice-cooling. The reaction mixture was then left to heat up to room temperature and stirred for a further 16 h. After the bis-methoxyamine 3 was completely consumed, water (20 ml) was added, the organic phase separated off and the aqueous phase extracted with diethyl ether (3×20 ml). The organic phases were combined, the solvent removed under vacuum and the crude product purified using column chromatography (silica gel, eluent chloroform/ethyl acetate 3:1). 1.1 g (79%) 1,6-bis(N-acryloyl-N-methoxyamino)hexane 4 was obtained. $^1$H-NMR (300 MHz, CDCl$_3$): δ=1.31-1.36 (m, 4H), 1.59-1.69 (m, 4H), 3.65 (t, J=7.2 Hz, 4H), 3.68 (s, 6H), 5.74 (dd, J=10.3, 2.1 Hz, 2H), 6.41 (dd, J=17.1, 2.1 Hz, 2H), 6.71 (dd, J=17.1, 10.3 Hz, 2H) ppm. $^{13}$C-NMR (75 MHz, CDCl$_3$): δ=26.4 (2CH$_2$), 26.9 (2CH$_2$), 44.9 (2CH$_2$), 62.1 (2CH$_3$), 126.2 (CH), 128.9 (CH$_2$), 166.1 (2C) ppm.

Example 2

Synthesis of [10-(N-acryloyl-N-methoxyamino) decyl]phosphoric acid (5)

1$^{st}$ stage: 10-hydroxydecyl-di-tert-butyl phosphate (6)

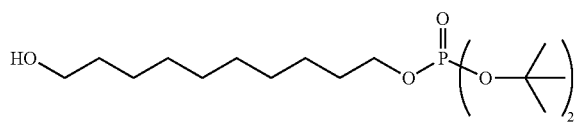

Anhydrous THF (400 ml) was added accompanied by stirring under nitrogen to a mixture of 1,10-decanediol (34.9 g, 200 mmol) and sodium hydride (8.1 g of a 60% suspension in mineral oil, 200 mmol). The reaction mixture was heated for 18 h under reflux. After the addition of di-tert-butylchlorophosphate (27 g, 118 mmol), which according to the literature (cf. H. Goldwhite, B. C) Saunders, *J. Chem. Soc.* 1957, 2409-2412; T. Gajda, A. Zwierzak, *Synthesis* 1976, 243-244) was obtainable in 2 stages from PCl$_3$ and tert-butanol, was heated for a further 1.5 h under reflux and the solvent then removed under vacuum. A mixture of tert-butyl methyl ether (MTBE, 400 ml) and water (100 ml) was added to the residue. After separation of the organic phase this was washed with a 10% NaCl solution and washed with saturated NaCl solution. It was then dried over anhydrous magnesium sulfate and the solvent removed. The residue was dissolved in some boiling MTBE. By adding 5 times the quantity of pentane, non-reacted decanediol could be crystallized out. After filtration the crude product was purified using column chromatography (silica gel, eluent: Chloroform/MTBE 8:1 to 3:1). 19.3 g (45%) 10-hydroxydecyl-di-tert-butyl phosphate 6 was obtained as a colourless, highly-viscous oil.

2$^{nd}$ stage 10-(methanesulfonyloxy)decyl-di-tert-butyl phosphate (7)

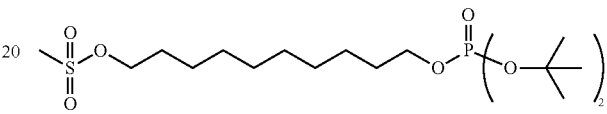

Freshly distilled mesylchloride (4.5 g, 39.3 mmol) was added dropwise accompanied by stirring over a period of 1 h to a solution of 10-hydroxydecyl-di-tert-butyl phosphate 6 (12.6 g, 34.4 mmol), triethylamine (5.5 ml, 39.5 mmol) and DMAP (=4-(dimethylamino)-pyridine) (220 mg, 1.8 mmol) in anhydrous methylene chloride (35 ml) such that the temperature of the reaction mixture remained between −5 and 0° C. This was then heated to room temperature, stirred for a further 1 h, the solvent removed under reduced pressure and a mixture of MTBE (=tert-butyl methyl ether) (100 ml) and water (50 ml) was added to the residue. This mixture was set to pH~5 with 10% H$_2$SO$_4$. The aqueous phase was extracted with MTBE (3×30 ml). The combined organic phases were washed with water (30 ml) and saturated NaCl solution (2×50 ml) and dried over anhydrous magnesium sulfate. The removal by distillation of the solvent resulted in 15.2 g 10-(methanesulfonyloxy)decyl-di-tert-butyl phosphate 7 as a slightly yellowish oil. $^1$H-NMR (CDCl$_3$, 250 MHz): δ=1.25-1.45 (m, 12H), 1.47 (s, 18H), 1.58-1.80 (m, 4H), 3.00 (s, 3H), 3.93 (q, J=6.6 Hz, 2H), 4.22 (t, J=6.6 Hz, 2H) ppm.

3$^{rd}$ stage: 10-methoxyaminodecyl-di-tert-butyl phosphate (8)

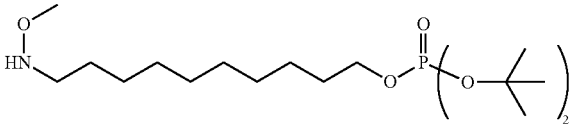

The mesylate 7 (15.2 g, 34.2) in acetone (5 ml) was added accompanied by stirring to a suspension of anhydrous NaI (6.85 g, 45.7 mmol) in dry acetone (30 ml). The mixture was stirred for 24 h at room temperature. The solvent was then removed and the residue was dispersed in a mixture of MTBE (100 ml), water (50 ml) and 100 mg Na$_2$S$_2$O$_4$. The organic phase was separated off and the aqueous phase was extracted with MTBE (3×30 ml). The combined organic phases were washed with water (30 ml) and saturated NaCl solution (2×50 ml) and dried over anhydrous magnesium sulfate. The solvent was then removed. The thus-obtained slightly yellowish liquid iodide (16.3 g, 34 mmol) ($^1$H-NMR (CDCl$_3$, 250 MHz): δ=1.25-1.46 (m, 12H), 1.48 (s, 18H), 1.64 (tt, J=6.8, 6.6 Hz, 2H), 1.81 (tt, J=7.0, 6.8 Hz, 2H), 3.18 (t, J=7.0 Hz, 2H), 3.93 (q, J=6.6 Hz, 2H) ppm) was dissolved in anhydrous THF (14 ml) and added to a suspension of methoxyamine (14.0 g, 297 mmol) and NaH (1.36 g of a 60% suspension in mineral oil, 34 mmol) in THF (20 ml) accompanied by stirring. The reaction mixture was heated for 16 h under reflux. After evaporating off the solvent under vacuum dry hexane was added to the residue and this was then stirred for 2 h. Filtration through a thin sheet of Celite® then took place and the solvent was removed. The crude product (12.4 g) was purified by flash chromatography (silica gel (450 ml), eluent chloroform/MTBE/ethyl acetate, 4:1:0 to 4:1:1), wherein 8.58 g (64%) of 10-methoxyaminodecyl-di-tert-butyl phosphate 8 was obtained. $^1$H-NMR (CDCl$_3$, 300 MHz): δ=1.22-1.40 (m, 12H), 1.47 (s, 18H), 1.45-1.55 (m, 2H), 1.64 (tt, J=6.8, 6.6 Hz, 2H), 2.90 (t, J=7.3 Hz, 2H), 3.53 (s, 3H), 3.93 (q, J=6.6 Hz, 2H), 5.53 (bs, 1H) ppm. $^{13}$C-NMR (CDCl$_3$, 75.5 MHz): δ=25.6 (CH$_2$), 27.2 (CH$_2$), 27.3 (CH$_2$), 29.2 (CH$_2$), 29.4 (CH$_2$), 29.5 (CH$_2$), 29.8 (CH$_3$), 29.9 (CH$_3$), 30.2 (CH$_2$), 30.3 (CH$_2$), 51.9 (CH$_2$), 62.8 (CH$_3$), 66.8 (CH$_2$), 66.9 (CH$_2$), 81.8 (C), 81.9 (C) ppm.

4$^{th}$ stage:
[10-(N-acryloyl-N-methoxyamino)decyl]phosphoric acid di-tert-butylester (9)

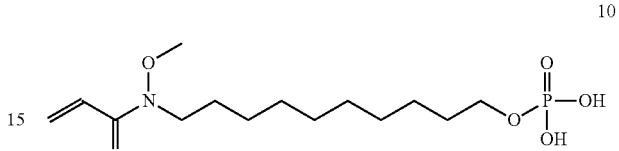

9

A solution of acrylic acid chloride (996 mg, 11 mmol) in CH$_2$Cl$_2$ (4 ml) was added dropwise accompanied by stirring over a period of 1 h to a solution of methoxyamine 8 (3.96 g, 10 mmol), triethylamine (1.53 ml, 11 mmol), DMAP (122 mg, 1 mmol) and BHT (10 mg) in CH$_2$Cl$_2$ (16 ml) such that the temperature of the reaction mixture remained between −5 and 0° C. After heating to room temperature, stirring took place for 16 h and then the solvent was distilled off under vacuum. A mixture of (50 ml) and water (25 ml) was added to the residue obtained. This mixture was set to pH ~5 with 10% H$_2$SO$_4$. After separating off the organic phase the aqueous phase was extracted with MTBE (3×20 ml). The combined organic phases were washed with water (20 ml) and saturated NaCl solution (2×25 ml) and dried over anhydrous magnesium sulfate. After the removal by distillation of the solvent an oil was obtained which was purified by flash chromatography (silica gel (100 ml), eluent chloroform/MTBE 6:1 to 3:1), wherein 3.19 g (71%) [10-(N-acryloyl-N-methoxyamino)decyl]phosphoric acid di-tert-butyl ester 9 was obtained as a weakly yellowish oil. $^1$H-NMR (CDCl$_3$, 250 MHz): δ=1.22-1.39 (m, 12H), 1.47 (s, 18H), 1.58-1.69 (m, 4H), 3.65 (t, J=7.4 Hz, 2H), 3.69 (s, 3H), 3.93 (q, J=6.6 Hz, 2H), 5.74 (dd, J=10.3, 2.0 Hz, 1H), 6.42 (dd, J=17.1, 2.0 Hz, 1H), 6.72 (dd, J=17.1, 10.3 Hz, 1H) ppm. $^{13}$C-NMR (CDCl$_3$, 75,5 MHz): δ=25.6 (CH$_2$), 26.7 (CH$_2$), 27.0 (CH$_2$), 29.1 (CH$_2$), 29.2 (CH$_2$), 29.3 (CH$_2$), 29.4 (CH$_2$), 29.8 (CH$_3$), 29.9 (CH$_3$), 30.2 (CH$_2$), 30.3 (CH$_2$), 62.1 (CH$_3$), 66.8 (CH$_2$), 66.9 (CH$_2$), 81.8 (C), 81.9 (C), 126.2 (CH), 128.9 (CH$_2$), 166.0 (C) ppm.

5$^{th}$ stage:
[10-(N-acryloyl-N-methoxyamino)decyl]phosphoric acid (10)

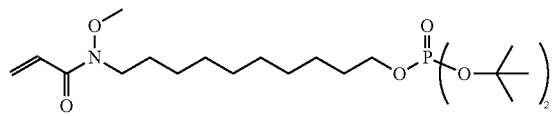

10

[10-(N-acryloyl-N-methoxyamino)decyl]phosphoric acid di-tert-butyl ester 9 (4.5 g, 10 mmol) was dissolved in tetrachlorocarbon (20 ml) and was added to this trifluoroacetic acid (3.07 g, 26.9 mmol). The reaction mixture was heated on the rotary evaporator (600-630 mbar) for 1 h to 50° C. and the pressure then reduced over 1 h to 5 mbar. The residue was then dried in the fine vacuum (approx. 0.03 mbar) until weight was constant, wherein 2.84 g (84%) [10-(N-acryloyl-N-methoxyamino)decyl]phosphoric acid 10 was obtained as a yellowish oil. $^1$H-NMR (CDCl$_3$, 300 MHz): δ=1.28-1.37 (m, 12H), 1.64-1.67 (m, 4H), 3.67-3.71 (m, 5H), 4.01 (q, 2H), 5.83 (dd, 1H), 6.42 (dd, 1H), 6.46 (m, 1H), 11.56 (s, 2H) ppm. $^{31}$P-NMR (DMSO-d$_6$, 162 MHz): δ=2.58 ppm.

Example 3

Radical polymerization of the bis(meth)acrylamide 4

In Schlenk flasks, solutions of 30% 1,6-bis(N-acryloyl-N-methoxyamino)hexane 4 from example 1 or 30% glycerol dimethacrylate were prepared as a comparative example and 1 mass-% 2,2'-azobis-(isobutyronitrile) (initiator) in chlorobenzene and degassed by passing through argon. The polymerization batches were then heated to 56° C. in a constant-temperature chamber. The time taken for a three-dimensional stable gel to form was measured as gelling time.

| Cross-linker | Gelling time |
|---|---|
| 1,6-bis(N-acryloyl-N-methoxyamino) hexane 4 | 80 s |
| Glycerine dimethacrylate (comparative example) | 7 min |

The example demonstrates the high reactivity of the grapevine cross-linkers in radical polymerization compared with commercial dimethacrylates.

Example 4

[10-(N-acryloyl-N-methoxyamino)decyl]phosphoric acid 10 Containing Dentine Adhesive from Example 3

To investigate the dentine adhesion on bovine tooth dentine an adhesive of the following composition (figures in wt.-%) was prepared:

| | |
|---|---|
| Strongly acid adhesive monomer 10$^{a)}$: | 11.1% |
| Glycerine dimethacrylate: | 11.0% |
| 2-hydroxyethyl methacrylate: | 20.0% |

| | |
|---|---|
| Ethanol: | 24.0% |
| Bis-GMA: | 33.1% |
| Photoinitiator: | 0.8% |

[a] [10-(N-acryloyl-N-methoxyamino)decyl]phosphoric acid

Bovine teeth were embedded in a plastic cylinder such that the dentine and the plastic were on one level. After 15 s etching with 37% phosphoric acid was followed by thorough washing with water. The dentinal tubules were opened by the acid etching. A layer of adhesive of the above composition was then applied with a microbrush, the solvent removed by operating the airbrush for a short time and lit for 40 s with a halogen lamp (Astralis 7, Ivoclar Vivadent AG). A composite cylinder of Tetric® Ceram (Ivoclar Vivadent AG) was then polymerized onto the adhesive layer in two layers each of 1-2 mm by 40 s lighting in each case with the halogen lamp Astralis 7. The test pieces were then stored in water for 24 h at 37° C. and the shearing adhesive strength measured at 17.0 MPa, which represents a very high coefficient of dentine adhesion for a non-optimized adhesive composition.

Example 5

[10-(N-acryloyl-N-methoxyamino)decyl]phosphoric acid 10 Containing Self-Adhesive Composite from Example 3

To investigate the dentine adhesion on bovine tooth dentine a composite of the following composition (figures in wt.-%) was prepared:

| | |
|---|---|
| Strongly acid adhesive monomer 10[a]: | 3.0% |
| UDMA | 5.7% |
| 2-acetoacetoxyethyl methacrylate: | 3.0% |
| Bis-GMA: | 8.0% |
| Photoinitiator[b]: | 0.3% |
| Fillers[c]: | 80.0% |

[a] [10-(N-acryloyl-N-methoxyamino)decyl]phosphoric acid
[b] Mixture of 0.1% camphorquinone and 0.2% 4-dimethylaminobenzoic acid ethyl ester
[c] Mixture of 39 wt.-% silanized Ba—Al-silicate glass filler and 41 wt.-% isofiller.

Embedded bovine teeth were used analogously to example 4. The dentine surface was firstly finely-(P120) then very finely-sanded (P600). A thin layer of the above-described composite was directly applied to this dentine surface and a composite cylinder of Tetric® Ceram (Ivoclar Vivadent AG) with a diameter of 4 mm was then pressed onto this. Then it was lit from all sides 4×20 s with the Astralis 7 halogen lamp. The test pieces were then stored in water for 24 h at 37° C. and the shearing adhesive strength measured at 7.2 MPa, which represents an excellent value for self-adhesion of a composite.

All numbers expressing quantities or parameters used in the specification are to be understood as additionally being modified in all instances by the term "about". Notwithstanding that the numerical ranges and parameters set forth, the broad scope of the subject matter presented herein are approximations, the numerical values set forth are indicated as precisely as possible. For example, any numerical value may inherently contain certain errors, evidenced by the standard deviation associated with their respective measurement techniques, or round-off errors and inaccuracies.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:
1. A dental material comprising
   (a) 1 to 95 wt. % of at least one polymerizable N,O functionalized acrylic acid hydroxamide of the general Formula (I):

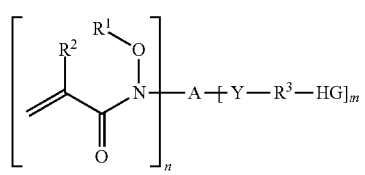

Formula (I)

in which
A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents,
Y is not present, or is O, S, an ester, amide or urethane group,
$R^1$ is hydrogen, an aliphatic $C_1$ to $C_{20}$ alkyl or $C_3$ to $C_8$ cycloalkyl radical which can carry one or more substituents,
$R^2$ is H or a $C_1$ to $C_{10}$ alkyl radical,
$R^3$ is not present or is a $C_1$ to $C_{16}$ alkylene radical which can be interrupted by O,
HG is not present, or is —COOH, —P=O(OH)$_2$; —P=O(OH)(OR$^4$); —O—P=O(OH)$_2$, —SO$_2$OH or —O—P=O(OH)(OR$^4$),
$R^4$ is a $C_1$ to $C_{15}$ alkyl radical, phenyl or benzyl radical,
n is a number from 2-5 and
m is 0,
   (b) 0 to 70 wt. % diluent monomer,
   (c) 0 to 70 wt. %, cross-linker monomer,
   (d) 0.1 to 5.0 wt. % polymerization initiator and
   (e) 0 to 80 wt. % filler,
   (f) 0 to 70 wt. % solvent, and
   (g) 0 to 70 wt. % adhesive monomer.
2. A dental material comprising
Formula (I):

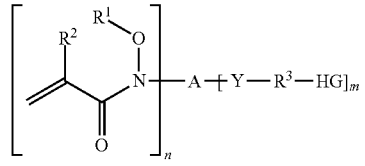

Formula (I)

in which
A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents,
Y is not present, or is O, S, an ester, amide or urethane group,
$R^1$ is hydrogen, an aliphatic $C_1$ to $C_{20}$ alkyl or $C_3$ to $C_8$ cycloalkyl radical which can carry one or more substituents,
$R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 2-5 and m is 0, (b) 0 to 70 wt. % diluent monomer,
(c) 0 to 70 wt. %, cross-linker monomer,
(d) 0.1 to 5.0 wt. % polymerization initiator and
(e) 0 to 80 wt. % filler,
(f) 0 to 70 wt. % solvent, and
(g) 0 to 70 wt. % adhesive monomer.

3. A dental material comprising Formula (I):

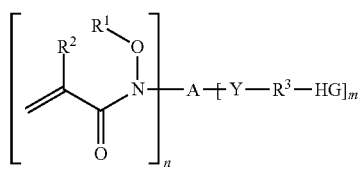

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 2-5 and m is a number from 2-3, (b) 0 to 70 wt. % diluent monomer,
(c) 0 to 70 wt. %, cross-linker monomer,
(d) 0.1 to 5.0 wt. % polymerization initiator and
(e) 0 to 80 wt. % filler,
(f) 0 to 70 wt. % solvent, and
(g) 0 to 70 wt. % adhesive monomer.

4. A dental adhesive comprising:

(a) 5 to 40 wt.-% acrylamide of the general Formula (I):

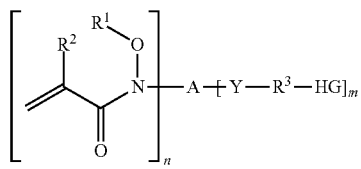

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1-5 and m is a number from 0-3, (b) 0 to 40 wt.-% diluent monomer,
(c) 0 to 70 wt.-% cross-linker monomer,
(d) 0.2 to 2.0 wt.-% polymerization initiator,
(e) 2 to 50 wt.-% solvent,
(f) 5 to 40 wt.-% adhesive monomer, and
(g) 0 to 20 wt.-% nanofiller (filler with a primary particle size of <50 nm).

5. A dental cement comprising:

(a) 5 to 20 wt.-% acrylamide of the general Formula (I):

Formula (I):

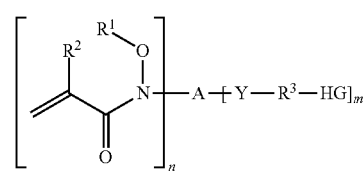

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1-5 and m is a number from 0-3, (b) 0 to 20 wt.-% diluent monomer,
(c) 0 to 20 wt.-% cross-linker monomer,
(d) 0.2 to 2.0 wt.-% polymerization initiator,
(e) 5 to 60 wt.-% filler, and
(f) 2 to 20 wt.-% adhesive monomer.

6. A dental filling material comprising:
(a) 5 to 20 wt.-% acrylamide of the general Formula (I):

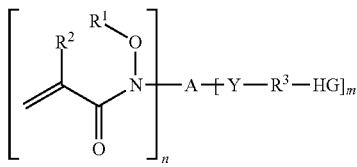
Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1-5 and m is a number from 0-3, (b) 0 to 30 wt.-% diluent monomer,
(c) 0 to 30 wt.-% cross-linker monomer,
(d) 0.2 to 2.0 wt.-% polymerization initiator, and
(e) 10 to 80 wt.-% solvent.

7. A dental coating material comprising:
(a) 5 to 40 wt.-% acrylamide of the general Formula (I):

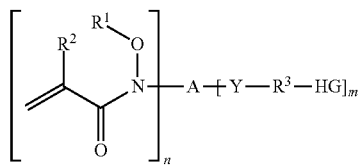
Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1-5 and m is a number from 0-3, (b) 0 to 50 wt.-% diluent monomer
(c) 0 to 50 wt.-% cross-linker monomer (d) 0.2 to 2.0 wt.-% polymerization initiator,
(e) 2 to 50 wt.-% solvent, and
(f) 0 to 20 wt.-% nanofiller (filler with a primary particle size of <50 nm).

8. A dental material comprising
(a) 1 to 95 wt. % of at least one polymerizable N,O functionalized acrylic acid hydroxamide of the general Formula (I):

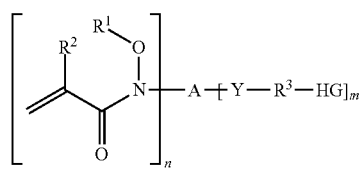
Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H or a $C_1$ to $C_{10}$ alkyl radical, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1 to 5 and m a number from 0 to 3, (b) 0 to 70 wt. % diluent monomer,
(c) 0 to 70 wt. %, cross-linker monomer,
(d) 0.1 to 5.0 wt. % polymerization initiator and
(e) 0 to 80 wt. % filler,
(f) 0 to 70 wt. % solvent, and
(g) 0 to 70 wt. % adhesive monomer.

9. The method of making a dental material, the method comprising:
(i) selecting a dental application material;
(ii) providing
(a) 1 to 95 wt.-% of at least one polymerible N,O-functionalized acrylic acid hydroxamide of the general Formula (I):

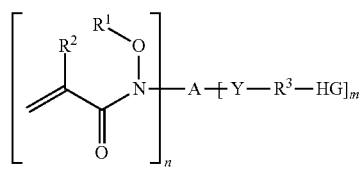
Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1 to 5 and m a number from 0 to 3, (b) 0 to 70 wt. % diluent monomer,
(c) 0 to 70 wt. %, cross-linker monomer,
(d) 0.1 to 5.0 wt. % polymerization initiator and
(e) 0 to 80 wt. % filler,
(f) 0 to 70 wt. % solvent, and
(g) 0 to 70 wt. % adhesive monomer (iii) selecting the value of at least one of the variables n or m to influence one or more of the functionality, cross-linking characteristics and adhesive properties of the dental material to tailor the properties of the material to optimize the performance thereof for the dental application; and (iv) compounding with other monomers, polymerization initiators, solvents or fillers to further tailor the properties of the material to optimize the performance thereof for the dental application.

10. A dental adhesive comprising:

(a) 10 to 40 wt.-% acrylamide of the general Formula (I):

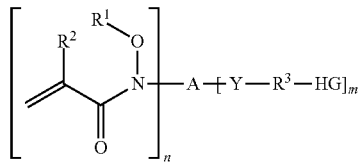

Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H, $R^3$ is not present or is a $C_1$ to $C_{16}$ alkylene radical which can be Ointerrupted by 0, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1 to 5 and m a number from 0 to 3, (b) 0 to 40 wt.-% diluent monomer,
(c) 50 to 70 wt.-% cross-linker monomer,
(d) 0.2 to 2.0 wt.-% polymerization initiator,
(e) 20 to 50 wt.-% solvent,
(f) 10 to 40 wt.-% adhesive monomer,
and
(g) 0 to 20 wt.-% nanofiller (filler with a primary particle size of <50 nm).

11. A dental filling material comprising:

(a) 5 to 20 wt.-% acrylamide of the general Formula (I):

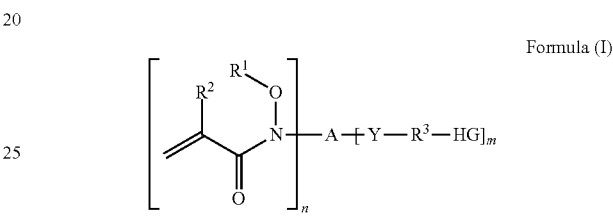

Formula (I)

in which

A is an n+m valent linear or branched aliphatic $C_1$ to $C_{50}$ radical, in which the carbon chain can be interrupted by O, S, —CO—O—, CO—NH, O—CO—NH or NH—CO—NH, an n+m valent aromatic $C_6$ to $C_{18}$ radical or an n+m valent cycloaliphatic or heterocyclic $C_3$ to $C_{18}$ radical, wherein the radicals can carry one or more substituents, Y is not present, or is O, S, an ester, amide or urethane group, $R^1$ is hydrogen, an aliphatic $C_1$ to $C_{20}$ alkyl or $C_3$ to $C_8$ cycloalkyl radical which can carry one or more substituents, $R^2$ is H, $R^3$ is not present or is a $C_1$ to $C_{16}$ alkylene radical which can be interrupted by O, HG is not present, or is —COOH, —P=O(OH)$_2$; —P=O(OH)(OR$^4$); —O—P=O(OH)$_2$, —SO$_2$OH or —O—P=O(OH)(OR$^4$), $R^4$ is a $C_1$ to $C_{15}$ alkyl radical, phenyl or benzyl radical, n is a number from 1 to 5 and m a number from 0 to 3, (b) 0 to 30 wt.-% diluent monomer,
(c) 0 to 30 wt.-% cross-linker monomer,
(d) 0.2 to 2.0 wt.-% polymerization initiator, and
(e) 50 to 80 wt.-% solvent.

* * * * *